(12) United States Patent
Worthley

(10) Patent No.: US 6,884,920 B2
(45) Date of Patent: Apr. 26, 2005

(54) HYDROCOLLOID WINDOW CATHETER DRESSING AND A METHOD FOR MAKING AND USING THE SAME

(75) Inventor: George Worthley, Wheaton, IL (US)

(73) Assignee: George Medical, L.L.C., Wheaton, IL (US)

( * ) Notice: Subject to any disclaimer, the term of this patent is extended or adjusted under 35 U.S.C. 154(b) by 306 days.

(21) Appl. No.: 10/083,938

(22) Filed: Feb. 27, 2002

(65) Prior Publication Data

US 2002/0123710 A1 Sep. 5, 2002

Related U.S. Application Data

(60) Provisional application No. 60/272,362, filed on Mar. 2, 2001.

(51) Int. Cl.[7] .................................. A61F 13/00
(52) U.S. Cl. .............................. 602/55; 602/41; 602/54; 602/56
(58) Field of Search .............. 602/41–59; 604/304–308, 604/180; 128/888–889

(56) References Cited

U.S. PATENT DOCUMENTS

| | | |
|---|---|---|
| 3,782,377 A | 1/1974 | Rychlik |
| 4,324,237 A | 4/1982 | Buttravoli |
| 4,534,762 A | 8/1985 | Heyer |
| 4,561,435 A | 12/1985 | McKnight et al. |
| 4,633,863 A | 1/1987 | Filips et al. |
| 4,669,458 A | 6/1987 | Abraham et al. |
| 4,678,462 A | 7/1987 | Vaillancourt |
| 4,917,112 A | 4/1990 | Kalt |
| 4,919,654 A | 4/1990 | Kalt |
| 4,966,590 A | 10/1990 | Kalt |
| 4,969,880 A | 11/1990 | Zamierowski |
| 4,973,314 A | 11/1990 | Garrett |
| 5,000,741 A | 3/1991 | Kalt |
| 5,074,847 A | 12/1991 | Greenwell et al. |
| 5,112,313 A | 5/1992 | Sallee |
| 5,160,315 A | 11/1992 | Heinecke et al. |
| 5,282,791 A | 2/1994 | Lipton et al. |
| 5,372,589 A | 12/1994 | Davis |
| 5,380,294 A | 1/1995 | Persson |
| 5,520,629 A | 5/1996 | Heinecke et al. |
| 5,569,207 A | 10/1996 | Gisselberg et al. |
| 5,599,289 A | 2/1997 | Castellana |
| 5,685,859 A | 11/1997 | Kornerup |
| 5,738,642 A | 4/1998 | Heinecke et al. |
| 5,776,106 A | 7/1998 | Matyas |
| 5,885,254 A | 3/1999 | Matyas |
| 5,980,497 A * | 11/1999 | Yavitz ........................ 604/294 |
| 6,124,520 A | 9/2000 | Roberts |
| 6,124,521 A | 9/2000 | Roberts |
| 6,149,614 A | 11/2000 | Dunshee et al. |
| 6,169,224 B1 | 1/2001 | Heinecke et al. |
| 6,273,873 B1 | 8/2001 | Fleischer |
| 6,322,539 B1 | 11/2001 | Cook |
| 6,592,888 B1 * | 7/2003 | Jensen et al. ................ 424/443 |
| 2001/0025159 A1 | 9/2001 | Fischer |

FOREIGN PATENT DOCUMENTS

EP          465023 A1 *   1/1992   ........... A61F/13/02

* cited by examiner

Primary Examiner—Kim M. Lewis
(74) Attorney, Agent, or Firm—Patents + TMS, P.C.

(57) ABSTRACT

A film dressing for wounds and/or catheter sites and a method for applying such a dressing and a process for making the same are provided. Preferably, the film dressing has a substantially clear top layer. The top layer may be a moisture vapor semi-permeable film. The moisture vapor semi-permeable film may be coated with an adhesive and may cover a window cut out of a semi-permeable tape border having an adhesive layer and a hydrocolloid silver adhesive. The dressing may further have liners for use in the application of the dressing to a patient.

27 Claims, 4 Drawing Sheets

HYDROCOLLOID WINDOW CATHETER DRESSING AND A METHOD FOR MAKING AND USING THE SAME

This application claims the benefit of U.S. Provisional Application Ser. No.: 60/272,362, filed Mar. 2, 2001.

BACKGROUND OF THE INVENTION

The present invention generally relates to a film dressing for wounds and/or intravenous catheter sites as well as a method for applying such a dressing and a process for making the same. More specifically, the present invention relates to a film dressing having a substantially clear top layer. The clear top layer may be a moisture vapor semi-permeable film. The moisture vapor semi-permeable film may be coated with an adhesive and may cover a window cut out of an adhesive semi-permeable tape border. The border may have a hydrocolloid silver adhesive. The dressing may further have removal liners for protection of the dressing and for use in the application of the dressing to a patient. The dressing of the present invention may be placed in a pouch and may be sterilized for use on a patient.

It is, of course, generally known to use transparent film dressings for the treatment and/or covering of wounds or intravenous catheter sites. Wound dressings that are adhered to human skin by pressure-sensitive adhesive have been known for many years. Such dressings are generally in the form of a sheet of film, foam, fabric or combination thereof. Known sheets have a pressure-sensitive adhesive layer for adhering the dressing to skin adjacent to the wound to secure the dressing in place. The pressure-sensitive adhesive layer may be configured to adhere to the skin surrounding the wound or to portions of skin surrounding the wound. In many dressings, the adhesive layer is substantially coextensive with the dressing and thus extends over the wound itself. In such dressings, the adhesives are intended to adhere to healthy skin outside the wound but not to the wound itself. Adhesives often do not adhere to or around the wounds due to inherent moisture associated with the wounds.

A further problem associated with these dressings includes adhesive oozing into score lines of casting sheets and/or score lines of the film, foam, or fabric sheet. For example, when applying a film dressing with score lines, after a scored portion of a layer is removed, adhesive may ooze into the score line. Another problem associated with these dressings includes keeping the wound clean and/or protected from bacteria or other harmful environmental conditions. Yet another problem associated with these dressings includes the difficult use and/or application of the dressing to the body. For example, when using a film dressing, the layers of the film dressing may wrinkle or stick together making the dressing difficult to apply.

A need, therefore, exists for a film dressing for wounds and/or intravenous catheter sites and a method for applying such a dressing and a process for making the same that is easy to use and protects the wound from exposure to harmful environmental conditions, such as bacteria or the like.

SUMMARY OF THE INVENTION

The present invention generally relates to a film dressing to cover a wound and/or catheter site and a method for applying such a dressing and a process for making the same.

To this end, in an embodiment of the present invention, a dressing is provided having a semi-permeable film, a semi-permeable tape border, and a hydrocolloid silver adhesive. The semi-permeable film has a top side and a bottom side. The semi-permeable tape border has a top surface, a bottom surface, a first edge and a second edge wherein the semi-permeable film covers the top surface of the semi-permeable tape border. The hydrocolloid silver adhesive is associated with the bottom surface of the semi-permeable tape border wherein the hydrocolloid silver adhesive forms a barrier.

In an embodiment, the dressing has an adhesive coating on the bottom side of the semi-permeable film.

In an embodiment, the dressing has an adhesive layer on the bottom surface of the semi-permeable tape border.

In an embodiment, the dressing has a first liner covering the adhesive layer opposite the semi-permeable tape border and covering the hydrocolloid silver adhesive wherein the first liner extends from the first edge of the semi-permeable tape border to a first location between the first edge of the semi-permeable tape border and the second edge of the semi-permeable tape border.

In an embodiment, the dressing has a tab extending from the first liner and folded onto the first liner.

In an embodiment, the dressing has a second liner covering the adhesive layer opposite the semi-permeable tape border and covering the hydrocolloid silver adhesive.

In an embodiment, the dressing has a window cut substantially through the semi-permeable tape border and hydrocolloid silver adhesive such that an opening is formed in the semi-permeable tape border and hydrocolloid silver adhesive.

In an embodiment, the opening of the hydrocolloid silver adhesive defines a perimeter around a wound.

In an embodiment, the semi-permeable film is moisture vapor permeable.

In an embodiment, the semi-permeable film is transparent.

In an embodiment, the semi-permeable film is constructed of polyurethane.

In an embodiment, the dressing has an antimicrobial additive associated with the hydrocolloid silver adhesive.

In an embodiment, the semi-permeable tape border is constructed of a non-woven material.

In another embodiment of the present invention, a method for applying a dressing having a semi-permeable film, a semi-permeable tape border, a hydrocolloid silver adhesive and a first liner to a patient is provided. The method comprises the steps of: exposing the dressing by removing the first liner; placing the exposed portion of the dressing on a patient such that the hydrocolloid silver adhesive adheres to the patient; and allowing the hydrocolloid silver adhesive to form a barrier.

In an embodiment, the method for applying a dressing further comprises the steps of providing a second liner; removing the second liner after removing the first liner and placing the exposed portion of the dressing on the patient; exposing a remaining portion of the dressing by removing the second liner; and applying the remaining portion of the dressing on the patient.

In an embodiment, the method for applying a dressing further comprises the step of cutting a window substantially through the semi-permeable film, the semi-permeable tape border and the hydrocolloid silver adhesive.

In an embodiment, the method for applying a dressing further comprises the step of folding the first liner to form a tab.

In an embodiment, the method for applying a dressing further comprises the step of gripping the tab and removing the first liner by pulling on the tab.

In another embodiment of the present invention, a process for manufacture of a dressing is provided. The process comprises the steps of: providing a semi-permeable tape border manufactured with an adhesive layer; cutting a window through the semi-permeable tape border and the adhesive layer; attaching a hydrocolloid silver adhesive on the adhesive layer of the semi-permeable tape border around a perimeter of the window; and forming a film on a top surface of the semi-permeable tape border.

In an embodiment, the process for applying a dressing further comprises the step of forming a first liner covering the semi-permeable tape border, the adhesive layer, and the hydrocolloid silver adhesive.

In an embodiment, the process for applying a dressing further comprises the step of folding the first liner to form a tab.

In an embodiment, the process for applying a dressing further comprises the step of forming a second liner on the semi-permeable tape border, the adhesive layer, the hydrocolloid silver adhesive and tab of the first liner.

It is, therefore, an advantage of the present invention to provide a dressing, a method for applying such a dressing and a process for making the same to use to cover a wound and/or a catheter site.

Another advantage of the present invention is to provide a dressing, a method for applying a dressing and a process for making the same that promotes moist wound healing.

Another advantage of the present invention is to provide a dressing, a method for applying a dressing and a process for making the same wherein the dressing is easy to use and to manufacture.

Yet another advantage of the present invention is to provide a dressing, a method for applying a dressing and a process for making the same wherein the dressing may be produced at a high rate of speed and/or inexpensive to manufacture.

Further, another advantage of the present invention is to provide a dressing, a method for applying a dressing and a process for making the same wherein a liner of the dressing is designed such that removal of the liner from the dressing may be accomplished without touching the adhesive coating or film layer.

Still further, another advantage of the present invention is to provide a dressing, a method for applying a dressing and a process for making the same wherein adhesive is prevented from oozing into score lines of casting sheets and/or score lines of the film, foam, or fabric sheet.

Another advantage of the present invention is to provide a dressing, a method for applying a dressing and a process for making the same wherein the dressing maintains the wound clean and protected from harmful environmental conditions, such as bacteria or the like.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention generally relates to a film dressing to cover a wound and/or a catheter site and a method for applying and making the same.

Figure 1:
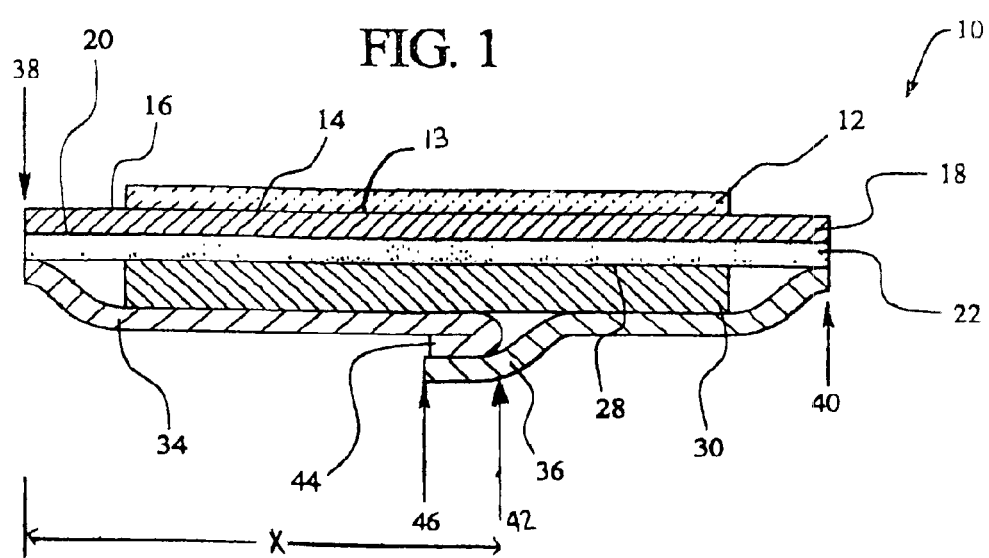
FIG. 1 is a cross-sectional view taken generally along the line I—I of FIG. 2 of an embodiment of a dressing of the present invention.
Figure 2:
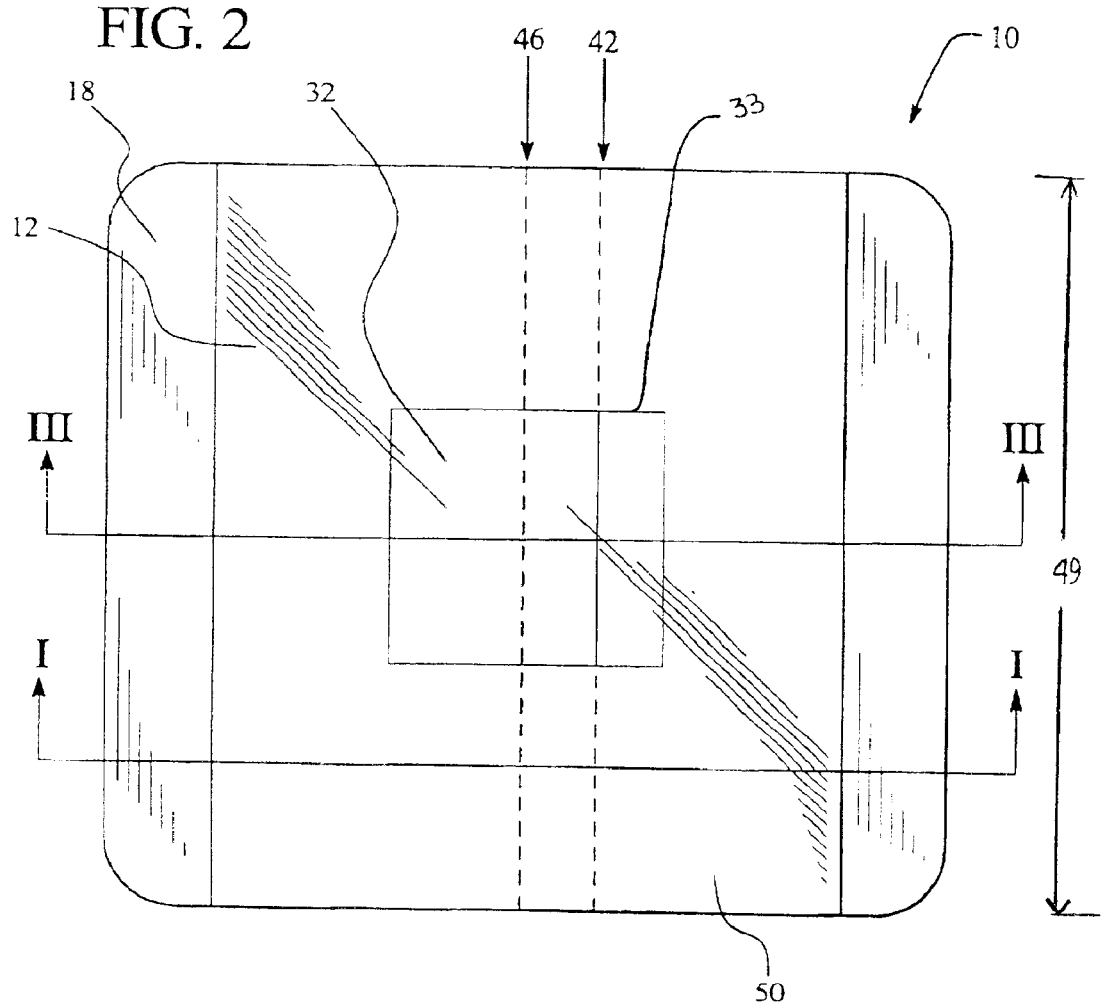
FIG. 2 is a top view of an embodiment of a dressing of the present invention.
Figure 3:
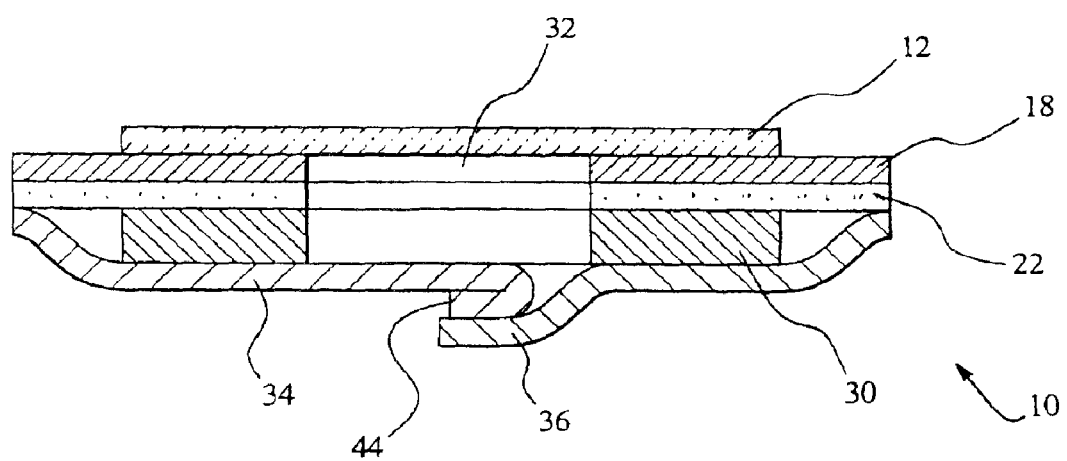
FIG. 3 is a cross-sectional view taken generally along the line III—III of FIG. 2 of an embodiment of a dressing of the present invention.

Referring now to the drawings wherein like numerals refer to like parts, FIGS. 1, 2 and 3 illustrate a dressing 10 of the present invention. As shown in FIGS. 1 and 3, the dressing 10 may have a number of layers. More specifically, the dressing 10 may have a semi-permeable film 12, a semi-permeable tape border 18 with an adhesive layer 22, a hydrocolloid silver adhesive 30, a first liner 34, and a second liner 36. Preferably, the semi-permeable film 12 is transparent.

The semi-permeable film 12 may have a bottom side 14 in substantial contact with a top surface 16 of the semi-permeable tape border 18. Further, the semi-permeable film 12 may have an adhesive 13 coated on the bottom side 14 wherein the bottom side 14 of the semi-permeable film 12 may be the skin contact side. The adhesive layer 22 may substantially be in contact with a bottom surface 20 of the semi-permeable tape border 18 and a top layer 28 of the hydrocolloid silver adhesive 30.

Referring now to FIGS. 2 and 3, the semi-permeable tape border 18, the adhesive layer 22, and the hydrocolloid silver adhesive 30 may have a window 32 such that the semi-permeable tape border 18, the adhesive layer 22, and the hydrocolloid silver adhesive 30 each form a frame. The window 32 may be formed by cutting through the semi-permeable tape border 18 and the adhesive layer 22 and forming the hydrocolloid silver adhesive 30 around a perimeter 33 of the window 32. The hydrocolloid silver adhesive 30 around the perimeter 33 of the window 32 may protect the wound and/or site from contamination. The semi-permeable film 12 may allow for viewing of the wound or catheter site through the window 32. The hydrocolloid silver adhesive 30 may contain, for example, an antimicrobial additive, such as, for example silver powder from HealthShield Technologies LLC.

Referring again to FIGS. 1, 2 and 3, a first liner 34 and a second liner 36 may be removably attached to the hydrocolloid silver adhesive 30 and the adhesive layer 22. The first liner 34 may extend from a first edge 38 of the dressing 10 to a distance "X" between the first edge 38 and a first point 42. The first liner 34 may fold back upon itself at the first point 42. As a result, the first liner 34 may form a tab 44. The first liner 34 may cover the adhesive layer 22 and the hydrocolloid silver adhesive 30 of the dressing 10. The second liner 36 extends from a second edge 40 of the dressing 10 to a point 46 beyond the tab 44 of the first liner 34. The first liner 34 and the second liner 36 may protect the adhesive layer 22.

In a preferred embodiment, a patient identification label and/or information label (not shown) may be laminated to one edge of the dressing for documentation purposes. Further, the semi-permeable film 12 may be constructed of polyurethane and/or may be moisture vapor permeable. The semi-permeable tape border 18 may be constructed of a non-woven polyester or similar non-woven material laminated on top with a semi-permeable film 12.

To use or otherwise apply the dressing 10, an individual may peel back the second liner 36 and then the first liner 34 to remove the same. After removal of the second liner 36 and the first liner 34, the individual may apply the exposed adhesive layer 22 of the semi-permeable tape border 18 to the wound and/or catheter site of a patient. Alternatively, the individual may remove the second liner 36 and place the exposed portion of the adhesive layer 22 of the semi-permeable tape border 18 to the wound and/or catheter site of the patient. After placing the exposed portion of the adhesive layer 22 of the semi-permeable tape border 18 on the patient, the individual may remove the first liner 34. After the first liner 34 is removed, the individual may place the remainder of the dressing 10 on the patient. Of course, the dressing 10 may be applied by the patient rather than by another individual.

Figure 4:
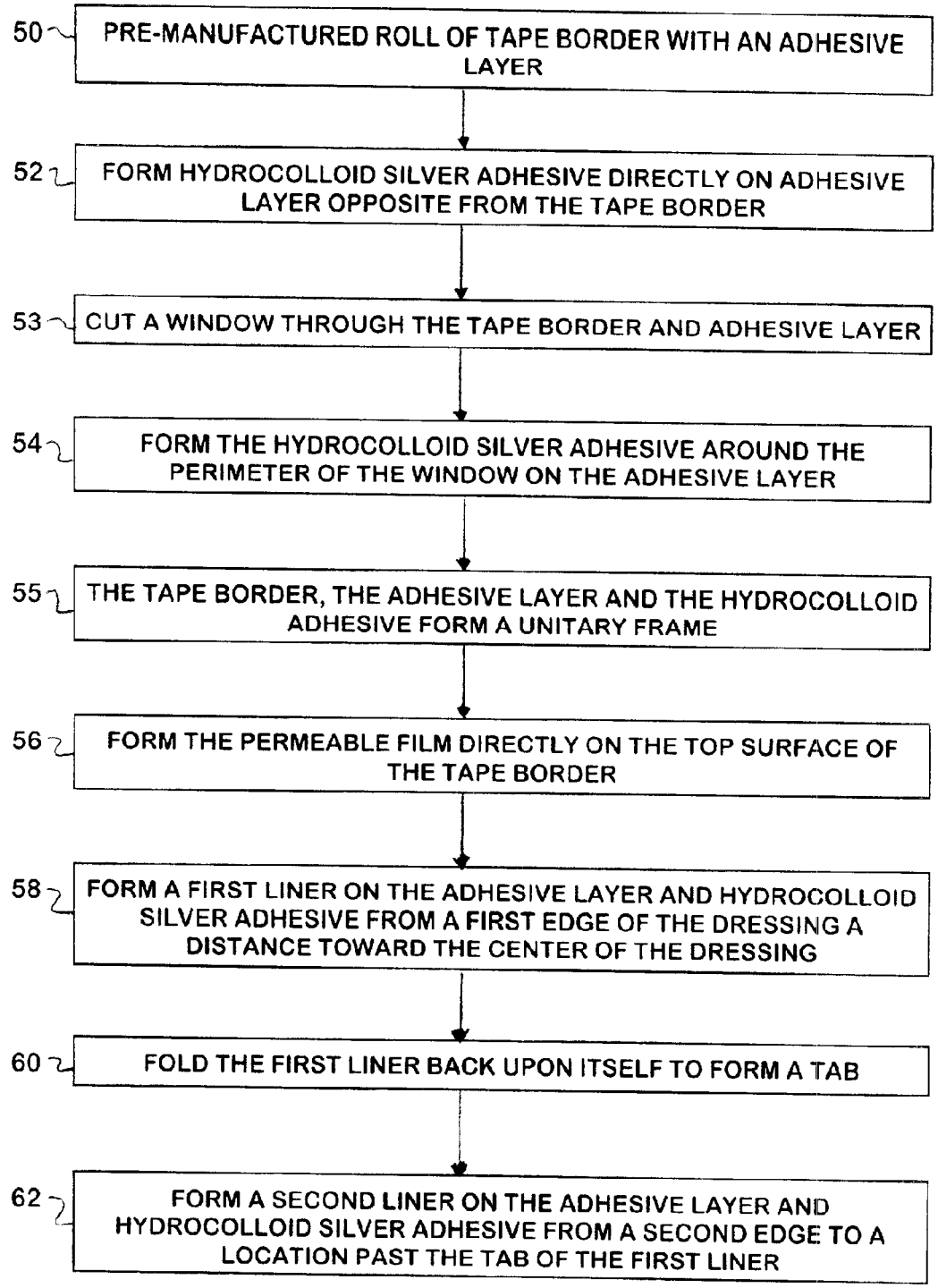
FIG. 4 is a flowchart illustrating an embodiment of a method for making a dressing of the present invention.

A flowchart illustrating an embodiment of a method to manufacture the dressing 10 of the present invention is generally illustrated in FIG. 4. A pre-manufactured roll of the semi-permeable tape border 18 with the adhesive layer 22 substantially covering the bottom surface 20 of the semi-permeable tape border 18 may be used as shown at step 50. The hydrocolloid silver adhesive 30 may be formed directly on the adhesive layer 22 opposite from the semi-permeable tape border 18 as shown at step 52. A window 32 may be cut through the semi-permeable tape border 18 and the adhesive layer 22 as shown at step 53. The hydrocolloid silver adhesive 30 may be formed on the adhesive layer 22 and around the perimeter 33 of the window 32 as shown at step 54. Accordingly, the hydrocolloid silver adhesive 30, the adhesive layer 22, and the semi-permeable tape border 18 may form a unitary frame as shown in step 55. The semi-permeable film 12 may be formed directly on the top surface 16 of the semi-permeable tape border 18 as shown at step 56. The semi-permeable film 12 substantially covers the window 32 and a length 49 of the dressing 10 as illustrated in FIG. 2.

The first liner 34 may be formed on the adhesive layer 22 and the hydrocolloid silver adhesive 30. The first liner may extend from the first edge 38 of the dressing to the first point 42, near center, of the dressing 10 as shown at step 58. The first liner 34 may be folded back upon itself at the first point 42 to form the tab 44 as shown at step 60. The second liner 36 may be formed on the adhesive layer 22 and the hydrocolloid silver adhesive 30 from the second edge 40 of the dressing 10 to a second point 46 of the dressing 10 as shown at step 62. No further measuring or scoring of the dressing 10 is required to implement the use of the dressing 10 for application to a patient.

The dressing 10, as shown in FIGS. 1–3, is square in shape. However, it should be appreciated that the dressing 10 may be any number of shapes and/or sizes including rectangles, circles, triangles, and the like.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A dressing comprising:
    a semi-permeable film having a top side and a bottom side;
    a semi-permeable tape border having a top surface, a bottom surface, a first edge and a second edge wherein the semi-permeable film covers the top surface of the semi-permeable tape border; and
    a hydrocolloid silver adhesive having a first side, a second side opposite to the first side and a perimeter wherein the first side of the hydrocolloid silver adhesive is covered by the bottom surface of the semi-permeable tape border; and
    a window in the semi-permeable tape border and the hydrocolloid silver adhesive wherein the window in the semi-permeable tape border is aligned with the window in the hydrocolloid silver adhesive wherein the window extends from the second side of the hydrocolloid silver adhesive to the semi-permeable tape border and further wherein the semi-permeable tape border extends outward with respect to the window beyond the perimeter of the hydrocolloid silver adhesive.

2. The dressing of claim 1 further comprising:
    an adhesive coating on the bottom side of the semi-permeable film.

3. The dressing of claim 1 further comprising:
    an adhesive layer on the bottom surface of the semi-permeable tape border.

4. The dressing of claim 3 further comprising:
    a first liner covering the adhesive layer opposite the semi-permeable tape border and covering the hydrocolloid silver adhesive wherein the first liner extends from the first edge of the semi-permeable tape border to a first location between the first edge of the semi-permeable tape border and the second edge of the semi-permeable tape border.

5. The dressing of claim 4 further comprising:
    a tab extending from the first liner and folded onto the first liner.

6. The dressing of claim 3 further comprising:
    a second liner covering the adhesive layer opposite the semi-permeable tape border and covering the hydrocolloid silver adhesive.

7. The dressing of claim 1 further comprising:
    a window cut substantially through the semi-permeable tape border and hydrocolloid silver adhesive such that an opening is formed in the semi-permeable tape border and hydrocolloid silver adhesive.

8. The dressing of claim 7 wherein the opening of the hydrocolloid silver adhesive defines a perimeter around a wound.

9. The dressing of claim 1 wherein the semi-permeable film is moisture vapor permeable.

10. The dressing of claim 1 wherein the semi-permeable film is transparent.

11. The dressing of claim 1 wherein the semi-permeable film is constructed of polyurethane.

12. The dressing of claim 1 further comprising:
    an antimicrobial additive associated with the hydrocolloid silver adhesive.

13. The dressing of claim 1 wherein the semi-permeable tape border is constructed of non-woven material and laminated with the semi-permeable film.

14. A method for applying a dressing having a semi-permeable film, a semi-permeable tape border having an adhesive, a hydrocolloid silver adhesive and a first liner to a site on a patient, the method comprising the steps of:
    exposing the dressing by removing the first liner; and
    placing the exposed portion of the dressing over the site of the patient wherein both the hydrocolloid silver adhesive and the semi-permeable tape border adhere to the patient wherein the hydrocolloid silver adhesive surrounds the site and further wherein the semi-permeable film covers the site wherein the site is visible through the dressing.

15. The method of claim 14 further comprising the steps of:

providing a second liner;

removing the second liner after removing the first liner and placing the exposed portion of the dressing on the patient;

exposing a remaining portion of the dressing by removing the second liner; and applying the remaining portion of the dressing on the patient.

16. The method of claim 14 further comprising the step of:

cutting a window substantially through the semi-permeable film, the semi-permeable tape border and the hydrocolloid silver adhesive.

17. The method of claim 14 further comprising the step of:

folding the first liner to form a tab.

18. The method of claim 17 further comprising the step of:

gripping the tab and removing the first liner by pulling on the tab.

19. A process for manufacture of a dressing, the process comprising the steps of:

providing a semi-permeable tape border manufactured with a bottom surface and a top surface opposite to the bottom surface wherein the bottom surface has an adhesive;

cutting a window through the semi-permeable tape border and the adhesive layer wherein the window has a perimeter;

attaching a hydrocolloid silver adhesive to the adhesive on the bottom surface of the semi-permeable tape border around the perimeter of the window wherein the semi-permeable tape border extends outward with respect to the window beyond the hydrocolloid silver adhesive; and forming a film on a top surface of the semi-permeable tape border wherein the film covers the window.

20. The process of claim 19 further comprising the step of:

forming a first liner covering the semi-permeable tape border, the adhesive layer, and the hydrocolloid silver adhesive.

21. The process of claim 20 further comprising the step of:

folding the first liner to form a tab.

22. The process of claim 21 further comprising the step of:

forming a second liner on the semi-permeable tape border, the adhesive layer, the hydrocolloid silver adhesive and tab of the first liner.

23. A dressing comprising:

a semi-permeable film having a top side, a bottom side opposite to the top side, a first edge and a second edge opposite to the first edge;

an adhesive layer covering the bottom side of the semi-permeable film;

a hydrocolloid silver adhesive layer attached to the adhesive layer wherein the hydrocolloid silver adhesive layer has a perimeter; and a window in the hydrocolloid silver adhesive layer and the adhesive layer wherein the window is within the perimeter of the hydrocolloid silver adhesive layer wherein the window in the hydrocolloid silver is aligned with the window in the adhesive layer and further wherein the adhesive layer extends outward with respect to the window beyond the perimeter of the hydrocolloid silver adhesive layer.

24. The dressing of claim 23 wherein the semi-permeable film is moisture vapor permeable.

25. The dressing of claim 23 wherein the hydrocolloid silver adhesive layer is antimicrobial.

26. The dressing of claim 23 further comprising:

a linear removably attached to the bottom side of the semi-permeable film and the hydrocolloid silver adhesive layer.

27. The dressing of claim 23 further comprising:

a tab on the linear wherein the tab extends outward with respect to the bottom side of the semi-permeable film.

* * * * *